(12) United States Patent
Wakamatsu et al.

(10) Patent No.: US 8,258,369 B2
(45) Date of Patent: Sep. 4, 2012

(54) METHOD FOR PREPARING FISH EMBRYOS

(75) Inventors: Yuko Wakamatsu, Nagoya (JP); Kenjiro Ozato, Nagoya (JP); Norihiko Ozato, legal representative, Saitama (JP)

(73) Assignee: National University Corporation Nagoya University, Nagoya-shi (JP)

( * ) Notice: Subject to any disclaimer, the term of this patent is extended or adjusted under 35 U.S.C. 154(b) by 91 days.

(21) Appl. No.: 12/224,284

(22) PCT Filed: Feb. 24, 2006

(86) PCT No.: PCT/JP2006/303447
§ 371 (c)(1),
(2), (4) Date: Nov. 25, 2008

(87) PCT Pub. No.: WO2007/096985
PCT Pub. Date: Aug. 30, 2007

(65) Prior Publication Data
US 2009/0255005 A1  Oct. 8, 2009

(51) Int. Cl.
*C12N 15/00* (2006.01)
*A01K 67/027* (2006.01)
(52) U.S. Cl. .......................................... 800/24; 800/20

(58) Field of Classification Search ..................... 800/24
See application file for complete search history.

(56) References Cited

OTHER PUBLICATIONS

Wakamatsu, 2008, Develop. Growth Differ., 50:427-436.*
Sun et al, 2005, Biology of Reproduction, 72:510-515.*
Ju et al, 2003, Develop. Growth Differ, 45:167-174.*
Lee et al, 2002, Nature Biotechnology, 20:795-799.*
Niwa et al, 2000, Cloning, 2:23-34).*
Bubenshchikova et al, Jan. 2006, Cloning and Stem Cells,7:255-264.*

* cited by examiner

*Primary Examiner* — Valarie Bertoglio
(74) *Attorney, Agent, or Firm* — Oliff & Berridge, PLC

(57) ABSTRACT

An object of the invention is to effectively prepare a fish embryo with a correct chromosomal ploidy by nuclear transplantation in which an exogenous fish nucleus is transplanted in a cytoplasmic recipient. For this object, the invention comprises a step of preparing a fish embryo by transplanting a fish cell nucleus to an unfertilized egg. The step of preparing a fish embryo comprises a step of imposing physical and/or chemical stress to the unfertilized egg after activation. By imposing such stress, the stage of haplosis in a female nucleus which happens at the early stage of a series of developmental steps occurring in an unfertilized egg is suppressed and the correct ploidy of an obtained embryo is at least secured.

19 Claims, 1 Drawing Sheet

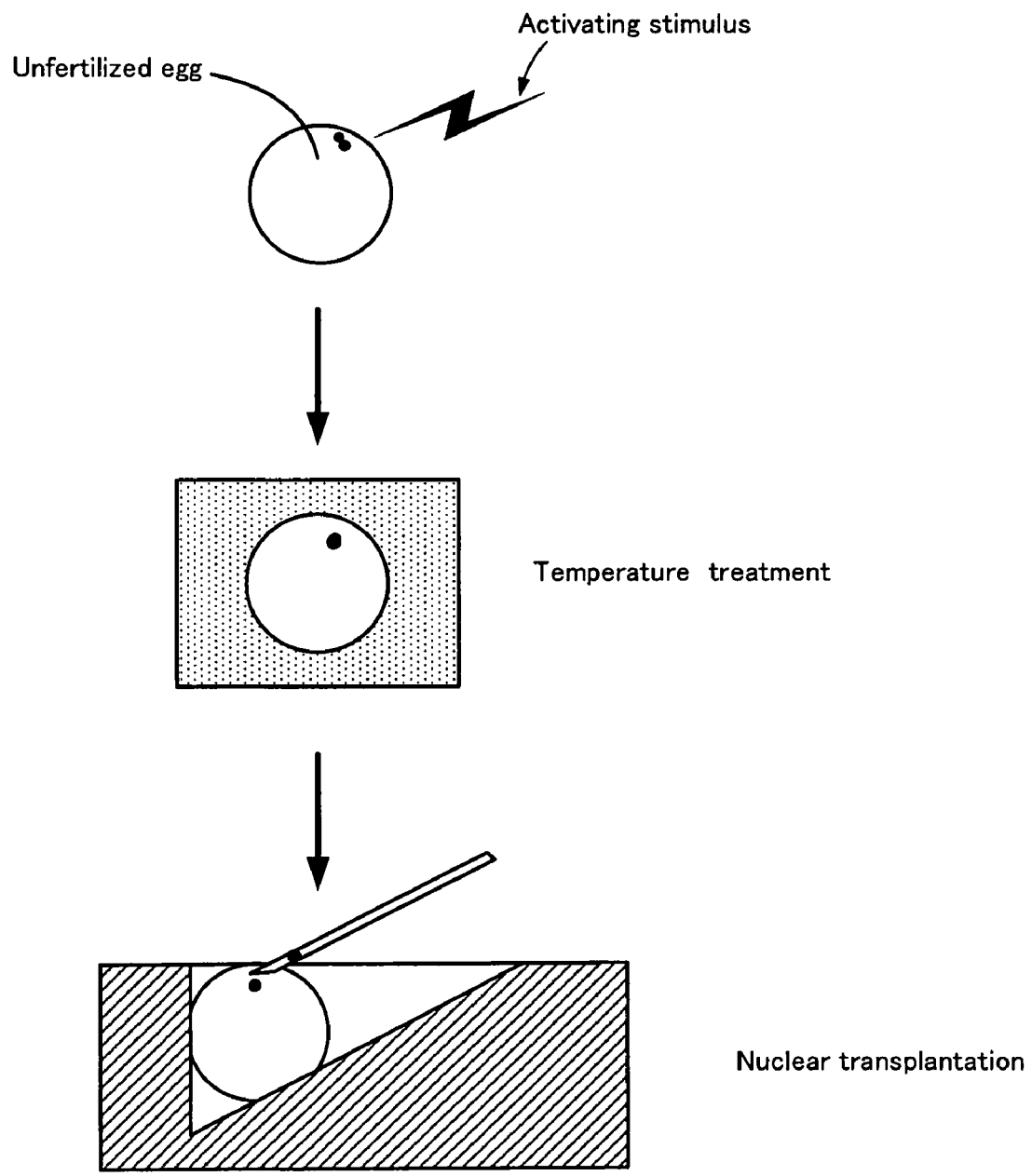

METHOD FOR PREPARING FISH EMBRYOS

BACKGROUND OF THE INVENTION

1. Field of the Invention

The present invention relates to a technology of preparing fish embryos and producing fish individuals.

2. Description of the Related Art

In recent years, clones have been produced in various mammals by transplanting a somatic cell-derived nucleus into each unfertilized egg. In fish, triploid individuals were reportedly produced by methods such as transplanting an embryonic cell into unenucleated unfertilized eggs that is used as the recipient cell (Niwa et al., CLONING, Vol. 2, Number 1, p. 23-24, 2000). Further, clones are reportedly produced in a method such as transplanting an embryonic cell into enucleated unfertilized egg that is used as recipient cell (e.g. Japanese Patent Application Publication 2002-125517; Wakamatsu et al., PNAS, vol. 98, no. 3, pp. 1071-1078, 2001).

On the other hand, for more efficient production of individuals or of genetically engineered modified individuals in fish, the development of a method for producing fish individuals by nuclear transplantation using cultured cell-derived or somatic cell-derived nuclei has been awaited. Under such circumstances, there is a report in which with zebra fish, individuals were reportedly produced by transplanting a nucleus of an embryo-derived cultured cell into each enucleated unfertilized egg (Ki-Young Lee et al., Nature Biotechnology 20, p. 795-799, 2002). Further, in medaka (*Oryzias laties*), an attempt has been made to produce individuals by transplanting a cultured cell nucleus into each unenucleated unfertilized egg (B. Ju et al., Develop. Growth Differ. 45, p. 167-174, 2003). However, in the latter report, it is disclosed that some embryos hatched but failed to mature into adult fish, and malformed embryos were often found although the extent of malformation varied and that embryo-constituting cells were mosaic with respect to the chromosomal ploidy thereof.

BRIEF SUMMARY OF THE INVENTION

Thus, in fish, unlike in mammals, no technology has been established as yet for stably constricting fish embryos maintaining a correct chromosomal ploidy by transplantation of somatic cell nuclei or cultured cell nuclei. In addition, it has not always been successful to obtain fertile individuals by such a technology.

Accordingly, it is an object of the present invention to efficiently prepare fish embryos with a correct chromosomal ploidy by nuclear transplantation comprising of transplanting an exogenous fish nucleus into each cytoplasmic recipient. Another object of the invention is to efficiently prepare fish embryos with the correct chromosomal ploidy by nuclear transplantation consisting in transplanting a somatic cell nucleus or cultured cell nucleus into each cytoplasmic recipient. A further object of the invention is to obtain fertile individuals by nuclear transplantation using fish somatic cell nuclei or cultured cell nuclei. A still further object of the invention is to prepare or produce fish embryos and individuals retaining a foreign DNA at a high rate by nuclear transplantation using somatic cell nuclei or cultured cell nuclei.

The present inventors paid their attention to recipient cells. In the unfertilized egg generally used as a recipient cell (unfertilized egg at a standstill in the metaphase in the second meiosis), there are two sets of female-derived chromosomes. In nuclear transplantation in fish, the unfertilized egg is generally activated by injection of the donor nucleus into the recipient cell, whereupon the developmental process is started; namely a series of developmental steps, including second polar body release, chromosome replication and cleavage, are started. In the second polar body release, one set out of the two sets of endogenous chromosomes occurring in the egg cell is eliminated from the egg.

The present inventors found that when the unfertilized egg after activation is exposed to a certain physical and/or chemical stress at an early stage of the series of developmental steps, at least the correct embryonic chromosomal ploidy can be secured. Based on this finding, the present inventors have completed the present invention. Furthermore, the inventors found that such recipient cell treatment makes it possible to efficiently prepare embryos with a correct ploidy by somatic cell nucleus or cultured cell nucleus transplantation and, as a result, obtain fertile individuals and, in addition, such treatment makes it possible to cause a foreign nucleus-derived gene to be expressed efficiently or preferentially. This finding has also led to the completion of the present invention. The present invention provides the following measures.

According to a first mode, the invention provides a method for preparing fish embryos which comprises a step of preparing a fish embryo by transplanting a fish cell nucleus into an unfertilized egg, whereas the aforesaid step of preparing a fish embryo includes a step of imposing physical and/or chemical stress on the unfertilized egg. In a mode of practice, the aforesaid treatment step may be the step including imposing, on the unfertilized egg, a physical and/or chemical stress that causes chromosomal diploidization in the unfertilized egg having started development or a physical and/or chemical stress equivalent to such degree. The treatment step may also be the step including imposing, on the unfertilized egg, a physical and/or chemical stress that inhibits or suppresses second polar body release. Further, the physical and/or chemical stress may include at least a stress due to the temperature of the environment surrounding the unfertilized egg.

Further, the above-mentioned treatment step may be the step including giving a stimulus that activates the unfertilized egg prior to imposing the physical and/or chemical stress. In this mode, the activating stimulation preferably involves no fish cell transplantation. Such unfertilized egg activating stimulus may be an electric stimulus.

Furthermore, the unfertilized egg to be fed in the treatment step preferably retains the endogenous nucleus. Further, it is preferred that such unfertilized egg is not subjected to any general enucleation treatment at any stage.

In such first mode, the cell that feeds the cell nucleus to be transplanted into the unfertilized egg is preferably selected from among somatic cells and cultured cells. Further, the cell nucleus feeding cell may be selected from among embryonic cells.

The first mode of the invention may further provide a method for preparing fish embryos which comprises a treatment step of imposing, on an endogenous nucleus-retaining unfertilized egg, a stimulus that activates the unfertilized egg, and imposing a physical and/or chemical stress that causes chromosome diploidization in the unfertilized egg that has started development or a physical and/or chemical stress equivalent to such degree, and a step of transplanting a fish somatic cell-derived or cultured cell-derived cell nucleus into the unfertilized egg after the treatment step.

In such first mode of the invention, the cell nucleus feeding cell may carry one or more members selected from among DNA mutations and foreign DNAs on a chromosome or chromosomes thereof. In any of the modes of configuration mentioned above, the fish may be selected from among fish species belonging to the genus *Oryzias* and relatives thereof. Further, the fish egg may be a diploid.

Furthermore, the individual obtained from the fish embryo may have a cell retaining only the chromosomes derived from a cell nucleus feeding cell, and the cell may retain only the chromosomes derived from the cell nucleus feeding cell transplanted is a germ cell.

Further, in the first mode thereof, the invention provides a method for preparing fish embryos, in which the treatment step includes giving a stimulus that activates the unfertilized egg to the unfertilized egg prior to imposing the physical and/or chemical stress thereon, the step may further include storing the unfertilized egg from after having been activated until the physical and/or chemical stress is imposed thereon under storage conditions that are laid down in advance. According to this method, the ploidy of the fish embryo to be obtained may be adjusted through the storage conditions that are determined in advance.

In a second mode, the invention provides a fish embryo as obtained by any of the above methods for preparing fish embryos.

Further, in a third mode, the invention provides a method for producing a fish individual. The method comprises a step or steps in the fish embryo preparation method as in any of the above method and a step of causing the prepared embryo to develop until hatching. In this mode of configuration, the method may further comprise a step of breeding the fish individuals that are produced.

In a fourth mode, the invention provides a fish individual as obtained by the method for producing fish individuals as in the above method for fish individual production. Further, in a fifth mode, the invention provides a cell of this fish individual.

In a sixth mode, the invention provides a method for producing a transgenic fish, which comprises a step of introducing a foreign DNA into a fish cell to thereby obtain a fish cell having the foreign DNA on a chromosome thereof, a step of preparing a fish embryo by transplanting the fish cell nucleus having the foreign DNA introduced on the chromosome thereof into an unfertilized egg and a step of causing the embryo to develop until hatching, and the fish embryo preparation step includes a treatment step of imposing a physical and/or chemical stress on the unfertilized egg.

In a seventh mode, the invention also provides a method for adjusting the ploidy of a fish embryo which comprises a method for adjusting the ploidy of a fish embryo to be prepared by giving an activating stimulus to an unfertilized egg, then imposing a physical and/or chemical stress on the unfertilized egg and transplanting a fish cell nucleus into the unfertilized egg. The method comprises a step of determining in advance conditions for storing the unfertilized egg from after having been activated until imposing the physical and/or chemical stress thereon.

In this mode of configuration, the storage conditions may be determined based on fish embryo ploidy data obtained by employing insemination with an untreated sperm as the activating stimulus, imposing the physical and/or chemical stress on the thus-obtained fertilized eggs and then causing embryogenesis therein without nuclear transplantation. The storage conditions are preferably laid down based on the yield of triploid fish embryos.

BRIEF DESCRIPTION OF THE DRAWINGS

FIG. 1 shows an example of the method for preparing a fish embryo by nuclear transplantation according to the invention.

DETAILED DESCRIPTION OF THE INVENTION

The fish embryo preparation method according to the invention is characterized in that it comprises the step of treating an unfertilized fish egg by giving a stimulus that activates the unfertilized egg and imposing a physical and/or chemical stress on the unfertilized egg. By carrying out such treatment step, fish embryos with a correct ploidy can be obtained efficiently. In the following, certain modes of practice of the invention are described in detail, referring to FIG. 1 and FIG. 2.

(Fish Embryo)

The term "fish embryo" is used herein to indicate a fish cell containing genetic materials capable of constructing a fish individual and occurring at any of all stages until fish individual hatching. The term "fish individual" as used herein includes, within the meaning thereof, not only an adult fish but also a fry or a young fish once it has hatched. The present invention is applicable at least to fish. The fish is not particularly restricted but includes, for example, zebra fish, medaka or killifish, goldfish, and dojo or loach, for research or experimental use. As for ornamental use, carp, crucian or gibel, medaka and goldfish, among others may be mentioned. As for edible purposes, salmon, trout, rainbow trout, brook trout or landlocked salmon, dwarf rill trout, eel, yellowtail, carp, flatfish, red sea bream, tilapia and so forth may be mentioned. Among them, fish species belonging to the genus *Oryzias*, including transparent medaka disclosed in Japanese Patent Application Publication 2001-346480, and relatives thereof are suited for use as various model fish species in researches and also for ornamental purposes. The fish to which the invention is applicable further includes fish already genetically modified either by natural mutation or artificially, and the invention is also useful in maintaining or further modifying the genetic characteristics of these modified fish.

(Unfertilized Egg)

In the practice of the invention, the unfertilized egg can serve as a recipient cell providing a fish embryo with cytoplasm in fish embryo preparation by nuclear transplantation. The unfertilized egg to be used in the practice of the invention is preferably an unfertilized egg at a standstill in the metaphase in the second meiosis (the so-called mature unfertilized egg). Such an unfertilized egg can be obtained by isolating from the ovary of a mature female individual or by incubating an oocyte in vitro until arrival of the metaphase in the second meiosis.

In carrying out the treatment step according to the invention, the unfertilized egg need not be enucleated but more preferably has the endogenous nucleus without undergoing enucleation. It is preferred that the procedure for enucleation of the unfertilized egg is avoided in the process for fish embryo preparation. This is because the conventional enucleation procedure tends to decrease the efficiency in fish embryo preparation. The term "enucleation" as used herein means the removal of the female-derived endogenous nucleus from the unfertilized egg by physical and/or chemical means. As the means for enucleation, irradiation with electromagnetic waves such as ultraviolet rays, suction of nucleus-containing cytoplasm by means of a micropipette and treatment with a chemical substance, among others may generally be employed.

(Cell Nucleus-Donating Cells)

The cell donating the fish cell nucleus to the unfertilized egg (hereinafter referred to as "donor cell" in short) provides the unfertilized egg, which is a recipient cell, with the nucleus. The donor cell is not particularly restricted provided that it contains at least those chromosome sets which are necessary for the development of an individual; thus, any one of embryonic cells and larva and adult somatic cells can be used. The time suited for the provision of the cell nucleus is not restricted, either; thus, the donor cell may be a diploid or tetraploid, but preferably is a diploid. The term "embryonic cell" as used herein includes, within the meaning thereof, cells at all developmental stages, from fertilized egg to hatching. The embryonic cell further includes embryonic stem cells as well as embryonic cells derived from primordial germ cells (gonocytes). As is evident from the foregoing, the donor cell includes not only undifferentiated cells but also differentiated cells. The donor cell may also be a syncytium-derived cell. Further, the donor cell is preferably a cultured cell, more preferably a cultured somatic cell.

As the donor cell, cells constituting various organs, for example fibroblasts, epithelial cells, endothelial cells, nerve cells, cartilage cells, myocardial cells, heart cells and liver cells as well as blood cells such as erythrocytes may be utilized. Such donor cells can be obtained by collecting from a part or the whole of the fish embryo or fish individual or by cultivating the cells thus collected.

It is not always necessary that the donor cell and the unfertilized egg be derived from the same fish species; it is preferred, however, that these be cells derived from the same fish species. As described later herein, the donor cell may contain, on chromosome(s) thereof, a DNA derived from a fish differing in species from the unfertilized egg and/or a DNA derived from another individual of the same fish species and/or a DNA derived from such a foreign organism as an animal other than fish and/or an artificial DNA.

(Cell Nucleus)

The cell nucleus to be donated to the unfertilized egg contains endogenous chromosomal DNAs intrinsic in the donor cell. The donor cell may have a naturally or artificially introduced mutation(s) on chromosome(s) thereof. The artificial mutation may have been introduced by a chemical or physical treatment or by homologous recombination. Further, the donor cell may have a foreign DNA on the chromosome(s) thereof. As the foreign DNA, among others, DNAs coding for the desired proteins, DNAs coding for selective markers and, further, DNAs coding for various regulatory regions, such as promoters and enhancers, and DNAs corresponding to RNA interference-causing RNAs may be mentioned. These foreign DNAs may be found randomly introduced on the chromosome(s) but, preferably, they are found introduced on the chromosome(s) by homologous recombination.

In the unfertilized egg, not only the donor cell's endogenous chromosomes but also such a nucleic acid as an extrachromosomal DNA and RNA occurring in the donor cell or nucleus may be transplanted by nuclear transplantation. Usable as such extrachromosomal nucleic acid are mutations or foreign DNAs that may be found provided on the chromosome(s) and, further, viruses, plasmids or artificial chromosomes. The donor cell may also contain RNA based on the morpholine antisense oligo technique and/or RNA or DNA based on the Caged compound technique. Such an extrachromosomal nucleic acid can be transplanted into the unfertilized egg, together with the chromosomes.

The donor cell having such a mutation and/or a foreign nucleic acid on a chromosome or extrachromosomally can be obtained by isolation from a fish that has undergone a natural mutation or from a genetically engineered fish, if necessary followed by cultivation. A mutation may also be introduced onto chromosome(s) by chemical and/or physical treatment of a cultured fish cell. Furthermore, it is also possible to obtain a fish cell containing a foreign nucleic acid on chromosome or extrachromosomally by introducing the foreign nucleic acid into a cultured fish cell by injection, cell fusion or any of various transfection techniques.

(Unfertilized Egg Treatment)
(Giving Activating Stimulus to Unfertilized Egg)

FIG. 1 shows a typical scheme in the fish embryo preparation method according to the invention. As shown in FIG. 1, an activating stimulus can be given to the unfertilized egg prior to imposing a physical and/or chemical stress thereon. The activating stimulus may be any one that can cause the unfertilized egg to start development. Such stimulus can be properly selected for use from among stimuli generally capable of causing gynogenesis to initiate in the unfertilized egg. As the method of stimulation, for example, electric stimulation by means of DC pulses, fertilization with a sperm inactivated by irradiation with ultraviolet rays, γ rays or X rays, contacting with a sperm extract, ethanol treatment, and calcium concentration adjustment may be employed. These stimuli may be applied singly, or two or more of them may be used in combination. Among them, electric stimulation is preferred. Electric stimulation is not only excellent in operability but also can be easily followed by the step of imposing a physical and/or chemical stress when such a stress is imposed in such subsequent step following stimulation. The electric stimulation conditions can be properly determined; for example, 25° C., 5 V, 50 microseconds, performed twice.

The unfertilized egg activation is not restricted to the case where such cell nucleus transplantation as mentioned above is involved but may also be effected by stimulation on the occasion of transplanting a cell nucleus into the unfertilized egg. Thus, the activation of the unfertilized egg may be accompanied by cell nucleus transplantation (introduction). This is because the transplantation of a cell nucleus into the unfertilized egg by any of the various methods to be mentioned later herein can generally activate the unfertilized egg.

In cases where the unfertilized egg activation is not accompanied by cell nucleus transplantation, it is preferred that the diploid state of the unfertilized egg be maintained until the introduction of a foreign cell nucleus while inhibiting the second polar body release or first cleavage. Presumably, the diploidization of the female recipient nucleus inhibits the ploidy of the developing embryo from becoming mosaic and makes it easy to obtain a fish embryo with a correct ploidy; however, this is merely an inference and will not limit the scope of the invention.

In the practice of the invention, such unfertilized egg activating stimulation is preferably given to an unenucleated unfertilized egg, namely an unfertilized egg retaining its endogenous nucleus. More specifically, the egg is an unenucleated unfertilized egg. By subjecting an unenucleated unfertilized egg to such treatment, it becomes possible for the female nucleus-retaining cytoplasm to receive the foreign cell nucleus and thus it becomes possible to prepare fish embryos with a high hatchability. Further, the stress imposition treatment carried out in the late stage of activation is considered to effectively adjust the initial stage of development of the unfertilized egg, making it possible to construct a fish embryo with a correct ploidy; though this is merely an inference, and will not limit the scope of the invention.

(Imposing Physical and/or Chemical Stress on Unfertilized Egg)

The physical and/or chemical stress against the unfertilized egg includes a physical and/or chemical stimulus showing an inhibitory action on the development initiating process in the unfertilized egg. The physical and/or chemical stimulus showing an inhibitory action on the development initiating process includes a physical and/or chemical stimulus that causes chromosome diploidization in the unfertilized egg that has started development, or a stimulus equivalent thereto in its degree. More specifically, it includes a physical and/or chemical stress which causes chromosome diploidization in the unfertilized egg that has started development, or such stress which does not cause chromosomal diploidization but suppresses the normal development starting process at a level lower than chromosome diploidization, for example suppresses or retards chromosome elimination by half. The term "development" as used herein includes, within the meaning thereof, parthenogenetic development. Such stress is preferably a stress suppressing or retarding chromosome elimination by half and promoting diploidization. A stress causing diploidization is more preferred.

Such physical and/or chemical stress is preferably such a stress that inhibits or suppresses either of second polar body release and first cleavage. While specific modes of such stress are diverse depending on the fish species, temperature treatment and pressure are common as the physical stress. As the chemical stress, treatment with cytochalacin B, high pH treatment and high concentration calcium treatment, among others may be utilized. These physical and chemical stresses may be imposed singly, or two or in combination may be imposed in combination.

As for the temperature treatment for inhibiting second polar body release, for instance, low temperature treatment is generally effective in many cases in fish species living in relatively high temperature areas, e.g. for red sea bream and flatfish, and, in fish species living in cool water, e.g. for salmon and trout species, high temperature treatment is effective in many cases. In red sea bream and flatfish, the treatment is carried out, 3-5 minutes after activation, in the vicinity of 0° C. for about 10-45 minutes; while in salmon and trout species, the treatment is carried out, at 10-60 minutes after activation, at 25-30° C. for about 10-20 minutes.

after activation a after ℓhaving been activated

In medaka, for instance, the temperature treatment can be started immediately or within 10 minutes after having been activated. This is because when the temperature treatment is started within this period, activation can be effected and the second polar body release induced thereby can be suppressed. The treatment is started preferably after the lapse of at least 1 minute, more preferably after the lapse of at least 2 minutes. After the lapse of at least 1 minute, activation can be secured and, after the lapse of at least 2 minutes, second polar body release can be effectively inhibited by the subsequent stress imposition. The temperature treatment is preferably started within 6 minutes after having been activated. Within 6 minutes, second polar body release can be suppressed by stress imposition. More preferably, the treatment is started within 4 minutes. Within 4 minutes, second polar body release can be effectively inhibited. Still more preferably, the treatment is started within the period of 2 minutes to 4 minutes after activation.

The temperature in the temperature treatment in medaka can be not lower than 37° C. and not higher than 45° C. This is because, within this range, second polar body release can be effectively suppressed. A temperature of 40° C. or higher is preferred. This is because, at 40° C. or higher, a treatment performed in short time period is effective. A temperature of 41° C. or higher is more preferred. Moreover, the temperature is preferably not higher than 43° C. This is because, with the temperature at 43° C. or lower, the subsequent embryogenesis is hardly inhibited. A temperature of 42° C. or lower is more preferred. Furthermore, the treatment time at such a temperature can be within 5 minutes. Within this range, the second polar body release can be suppressed without suppressing the subsequent fish embryogenesis. The treatment time is more preferably within 4 minutes, and still more preferably 2 to 3 minutes.

Further, the temperature in the temperature treatment in medaka can be not lower than −5° C. and not higher than 15° C. Even within this range, second polar body release can be suppressed. In cases where the treatment is carried out at a temperature of 0° C. or lower, a medium which will not freeze at that temperature is used for the treatment. The temperature is preferably not lower than 0° C. but may be in the vicinity of 0° C. so long as the medium does not freeze at the laid-out temperature. The temperature is preferably not higher than 10° C., and more preferably not higher than 5° C.

Appropriate conditions for such inhibition of second polar body release in various fish species can be found, e.g. by adequately combining the lapse of time after activation, treatment conditions such as temperature or pressure conditions and treatment time and by employing chromosome staining and/or flow cytometry.

As for the temperature treatment for inhibiting first cleavage, high temperature treatment and high water pressure treatment are said to be generally effective. In red sea bream, for example, the treatment is carried out, after the lapse of at least 46 minutes after activation, at 700 kg/cm$^2$ for 5 minutes and 30 seconds; in flatfish, after the lapse of at least 60 minutes after activation, at 650 kg/cm$^2$ for 6 minutes; in rainbow trout, after the lapse of 180-300 minutes after activation, at 28-32° C. for 4-10 minutes; and, in carp, after the lapse of at least 28-30 minutes after activation, at 40° C. for 2 minutes. Although the conditions for such first cleavage inhibition are diverse depending on the fish species, appropriate conditions can be learned e.g. by adequately combining the lapse of time after activation, treatment conditions such as temperature or pressure conditions and treatment time and by employing chromosome staining and/or flow cytometry.

As already mentioned hereinabove, the activating stimulation of the unfertilized egg is a prior condition for such inhibition or retention of second polar body release or first cleavage; however, there can be cases where it is not necessary for activating stimulation to precede stress imposition and there can be cases where an activating stimulus may be given under stress imposition. As regards to the order of activating stimulation and such stress disposition and nuclear transplantation, there are, for example, the following combinations.

(1) Activating stimulation without nuclear transplantation is followed by stress disposition and simultaneous or subsequent nuclear transplantation.
(2) Activating simulation without nuclear transplantation is followed by nuclear transplantation, which is further followed by stress disposition.
(3) Activating stimulation involving nuclear transplantation and simultaneous or subsequent stress disposition.

Among such various combinations, the combination (1) mentioned above, in particular activating stimulation followed by the above-mentioned stress disposition and the subsequent cell nucleus transplantation (cf. the scheme shown in FIG. 1) is most effective in effectively adjusting the early developmental stage of the unfertilized egg and construct a fish embryo with a correct ploidy.

(Storing Step after Unfertilized Egg from after Activating Stimulation Until Stress Disposition)

The storage conditions after unfertilized egg from after activating stimulation until the above-mentioned stress disposition may sometimes influence the preparation of a fish embryo with a correct or intended ploidy. Thus, the ploidy of the fish embryo to be obtained can be effectively controlled by adjusting the storage conditions in the storing step that is performed from after unfertilized egg activating stimulation is carried out until stress disposition is to be carried out. Therefore, a fish embryo with a correct or intended ploidy can be efficiently obtained by properly selecting the storage conditions. It is presumed that the storage conditions after stimulation until stress disposition influence the second polar body release-suppressing or first cleavage-inhibiting or suppressing effect of stress disposition; however, this speculation should not be construed as limiting the scope of the invention.

The storage conditions can be specified in terms of temperature and time. Such storage conditions can be established by widely varying the waiting time and temperature during the time from unfertilized egg activating stimulation to stress disposition, carrying out stress disposition, nuclear transplantation and embryo preparation, and selecting the conditions under which the largest number of embryos with an intended or correct ploidy (e.g. diploids) can be obtained. For efficiently establishing the storage conditions, it is also possible to give an activating stimulus by insemination using untreated sperms (original monoploid sperms), store the eggs under various conditions, then impose stress thereon, prepare embryos without nuclear transplantation and select the conditions under which fish embryos with a ploidy calculated by adding the numerical value "1" to the intended or correct ploidy can be obtained in the highest yield. When diploid fish embryos for example are intended, those storage conditions are employed under which triploid fish embryos can be obtained in the highest yield in the experiment carried out in the above-mentioned manner. By using insemination with untreated sperms as an activating stimulus, it becomes possible to obtain fish embryos in a high yield and, as a result, improve the reliability of the storage conditions established; in addition, it has been revealed that the thus established storage conditions can be applied to ploidy adjustment in unfertilized eggs given an original activating stimulus (activating stimulus for gynogenesis or activating stimulus for nuclear transplantation).

In the case of medaka (*Oryzias latipes*), for example, the storing step is preferably carried out within the range of not shorter than 2 minutes and not longer than 3 minutes after activating stimulation and a preferred temperature is 25° C., as mentioned later herein in the example section. More preferably, the storing step is carried out within the range of not shorter than 2 minutes and 30 seconds and not longer than 2 minutes and 45 seconds, whereby fish embryos with a correct ploidy (diploids) can be obtained.

(Nuclear Transplantation)

A fish embryo is prepared by transplanting a donor cell-derived cell nucleus into an unfertilized egg. As for the timing of transplantation of the donor nucleus into the unfertilized egg, various timings such as mentioned above can be selected; while it may be simultaneous with unfertilized egg activating stimulation, it is preferred that the transplantation is carried out after activating stimulation without cell nucleus transplantation. More preferably, the transplantation is carried out after activating stimulation without cell nucleus transplantation and after stress disposition. By doing so, it becomes possible to efficiently obtain fish embryos with a correct chromosomal ploidy, and, in addition, obtain fish embryos and individuals having, at a high rate, cells dominantly containing donor cell chromosomes.

The nuclear transplantation can be carried out by any of the methods known in the art, without particular restriction. As for the techniques, for example, cell fusion via a chemical substance, viral or electric technique, intact or damaged cell injection, dissolved cell injection, and nucleus injection can be employed. These nuclear transplantation techniques can induce and start the development in unfertilized eggs whether they are inactivated unfertilized eggs or after activation and the above-mentioned stress disposition. For example, donor cell injection by microinjection using a micromanipulator is sufficiently stimulating in inducing the development in unfertilized eggs after the above-mentioned stress disposition.

In preparing a transgenic fish, it is also possible to introduce a DNA construct (including various vectors such as plasmid vectors) containing a desired DNA into the fish embryo prepared. As the DNA to be contained in the DNA construct, a DNA coding for a desired protein, a DNA coding for a selective marker and, further, DNAs coding for various regulatory regions such as a promoter and an enhancer, and a DNA corresponding to an RNA causing RNA interference, among others may be mentioned. For such DNA construct introduction into the embryo, microinjection as well as transfection and other methods known in the art can be employed. Further, into the donor cell, there may be introduced an RNA based on the morpholine antisense oligo technique or an RNA based on the Caged technology.

(Fish Embryo Cultivation)

The thus-obtained fish embryo is cultivated for development until hatching under conditions appropriate for the fish species. The cultivation conditions for development until hatching can be properly selected according to the fish species. In the case of medaka, for instance, the cultivation is carried out at about 18° C. for about 24 hours after nuclear transplantation and, thereafter, the cultivation can be carried out at a temperature of about 26° C. A balanced salt solution (BSS) containing methylene blue or the like solution can be used as the culture medium. A fish individual can be obtained by causing the fish embryo to hatch in the above manner. The fish individual obtained can be bred by a method suited for the fish species. It is also possible to carry out further genetic modification by mating or chromosome manipulation.

According to the present invention described hereinabove, it is possible to obtain, by nuclear transplantation, fish embryos and fish individuals having a correct chromosomal ploidy and retaining donor-derived DNAs. According to the invention, the mosaicism with respect to the chromosomal ploidy is avoided and the chromosomal ploidy which is correct for the fish embryo and fish individual concerned is maintained. Since the fish chromosomes are diploid in number, embryos and individuals diploid in number of chromosomes are obtained. The fish individuals obtained according to the invention have normal reproductive cells and have fertility as well.

The fish embryos and individuals provided by the present invention retain donor cell-derived chromosomal DNAs. It has been confirmed that when the gene expression on a donor-derived chromosome is visualized using GFP (green fluorescent protein gene) as a foreign DNA integrated in the donor chromosome, the GFP is expressed in the fish embryos and individuals in the same mode as in the donor line. As indicated by such gene expression mode and the above-mentioned chromosomal ploidy, the fish embryos and fish individuals provided by the invention are fish embryos and fish individuals retaining donor chromosomes as ones dominant over unfertilized egg-derived chromosomes or in the form close to clones of the donor or in the form of clones. Furthermore, since the GFP gene is expressed in the same mode as in the donor line also in the $F_1$ generation obtained by mating a fish embryo according to the invention with an individual of the line from which the recipient of that fish individual was derived, the fish individual retains the donor chromosomes as dominant ones or the donor chromosomes alone in the reproductive cells as well.

Further, in the case of a foreign DNA or a mutation occurring on a donor nucleus chromosome, or in the case of introduction of a foreign nucleic acid such as a DNA construct into fish embryos, the fish embryos and fish individuals according to the invention occur as transgenic fish (including knockin, knockout and knockdown fish) in which the gene product encoded by such DNA is expressed. Since somatic cells and cultured cells are readily subjected to genetic engineering modifications, the invention makes it possible to obtain genetically engineered modified fish embryos and individuals with ease. According to the invention, a method for producing such transgenic fish is also provided which comprises the step of introducing a foreign DNA into a fish cell to thereby obtain a fish cell having the foreign DNA on chromosome, the step of transplanting the nucleus of the fish cell with the foreign DNA introduced on the chromosome into an unfertilized egg to prepare a fish embryo and the step of causing the fish embryo to develop until hatching, wherein the above-mentioned fish embryo preparation step comprises the step of imposing a physical and/or chemical stress on the unfertilized egg.

Furthermore, while it is possible, by breeding the fish individuals obtained, to increase the number of the offspring of those fish individuals, it is possible to obtain, from a fish individual once produced, clones of this fish individual or modification thereof easily by such chromosome manipulation for gynogenesis or the like that is applied to fish in general. Further, the results of a mating test using the fish individuals obtained in accordance with the invention indicate that the reproductive cells of the fish individuals according to the invention retain the donor chromosomes as dominant ones or the donor-chromosomes alone or in a mode close thereto.

According to the fish embryo and individual production method of the invention, the fish species that needs to be preserved and the traits thereof that needs to be preserved can be preserved. Further, since transgenic fish can be easily produced, the invention not only enables fish species improvements and increased fish production but also makes it possible to easily produce model fish in toxicology, various disease model fish and environmental monitoring fish for monitoring endocrine disrupting chemical substances, thus providing useful tools for gene expression analysis, new drug development and environment evaluation.

Furthermore, cells of such fish individuals can be used in various fields of researches and medical treatments. The cells of fish individuals may include somatic cells, germ cells, reproductive cells and, further, tissues, organs and internal organs, which are aggregates of the cells.

EXAMPLE 1

The following examples illustrate the invention more specifically. The following examples are, however, by no means limitative of the scope of the invention. In this example, nuclear transplantation was carried out using embryonic cells of medaka (*Oryzias latipes*) and cultured cells derived from somatic cells thereof. In Experiments 1 and 2, nuclear transplantation was carried out using orange-red medaka obtained by gene transfer using the β-actin-cassette-EGFP gene as the donor and orange-red medaka (hereinafter referred to as "OR") of an outbred strain as the recipient. The individuals obtained by nuclear transplantation were evaluated in sex, chromosomal ploidy, and GFP fluorescence and GFP gene detection and further subjected to test mating with the recipient OR. The $F_1$ generation obtained by the mating test was observed from the growth viewpoint and evaluated with GFP fluorescence and GFP gene detection.

1. Nuclear Transplantation

The donor β-actin-cassette-EGFP strain is a strain obtained by introducing, into OR, a fusion gene prepared by inserting the EGFP gene between a site about 2050 bp upstream of the site of translation initiation of the medaka β-actin gene and the trailer sequence (about 800 bp just behind the termination codon) and is homozygous with respect to the gene introduced. The gene transfer has been carried out in the following manner.

Based on the DNA base sequence of the medaka β-actin gene as described by Takagi et al. (Mol. Mar. Biol. Biotechnol. 3: 192-199, 1994), the trailer sequence (about 800 bp just behind the termination codon) was amplified from the genomic DNA of OR by PCR (primers: act3'-FW and act3'—RV, shown below), excised using NotI/NdeI and inserted into pEGFP (6077-1, Clontech) at the NotI site thereof. Then, about 2050 bp from the translation initiation site was amplified by PCR (primers: act5'-FW and act5'—RV, shown below) and then inserted into the pEGFP (6077-1, Clontech) at the SphI/KpnI site thereof. Thus was constructed a fusion gene (β-actin-cassette-EGFP) having the structure of β-actin(5')-EGFP-β-actin(3'). Then, prior to the first cleavage, the plasmid p-β-Act-cassette-EGFP was introduced into the cytoplasm of each fertilized egg of OR by microinjection. Homozygotes with respect to the β-actin-cassette-EGFP were produced by test mating of the transgenic fish. In such transgenic fish, the GFP fluorescence was observed in the whole body from the gastrula stage.

```
act3'-FW:
                                          (SEQ ID NO: 1)
CTGTAGCGGCCGCACAGACTTTCTCTCCTCCCCAG act3'-RV:
                                          (SEQ ID NO: 2)
TGCGTCTAGACGCATATGTTAAGCTTTAAAGAATCAATGGA act5'-FW:
                                          (SEQ ID NO: 3)
TATGGCATGCCATATGGTGAATGTATAGTAGCGTA act5'-RV:
                                          (SEQ ID NO: 4)
TCAAGGTACCAAGAATTCGGCTAAACTGGAAAAGAACA
```

(Recipient)

In each of Experiment 1 and Experiment 2, OR without gene transfer was used as the recipient. OR is medaka of an outbred strain with an orange-red body color and sexually matures in 1.5 months.

(Breeding Conditions)

The breeding of the donor and recipient mentioned above was carried out in aquaria in a breeding room maintained at 26° C. with the illumination adjusted so as to repeat a light-dark cycle consisting of a 14-hour light period and a 10-hour dark period. The feed given consisted of brine shrimp larvae (Ocean Star International, Snowville, N.H., USA) and a powder feed (Otohime β1, product of Nisshin Feed Inc.).

(Donor Cell Preparation)

In this nuclear transplantation, four-somite stage embryo cells were used as donor cells in Experiment 1 and, in Experiment 2, cultured adult caudal fin cells. The four-somite stage embryo cells were obtained by dissociating embryonic bodies at the same stage by pipetting in calcium- and magnesium-free phosphate-buffered saline (CMF-PBS) containing 0.03% trypsin and 0.04% EDTA and centrifuging the cell suspension obtained. The adult caudal-fin cells were obtained by collecting adult donor caudal fins, cutting them into small pieces, and cultivating them on gelatin-coated plastic culture dishes using a culture medium prepared by adding 20% of fetal calf serum to Leibovitz's L-15 medium in the air at 25° C. for 6-10 days. The cultured cells were rinsed with CMF-PBS and then treated with CMF-PBS containing 0.1% trypsin and 0.01% EDTA for separation into single cells. The cell suspension obtained was centrifuged at 50×g at 4° C. for 5 minutes.

The respective donor cells obtained in pellet form were resuspended in Leibovitz's L-15 medium and stored at 4° C. until use.

(Unfertilized Egg Preparation)

Female fishes that have been laying eggs everyday were transferred to an isolation tank for isolation on the day before experiment. On the day of experiment, they were dissected within 1-2 hours from the start of the light period and mature unfertilized eggs (unfertilized eggs) were recovered from ovaries and stored until use in a 35-mm plastic dish for suspension culture (Falcon (trade name), Becton Dickinson, Lincoln Park, N.J., USA) at 18° C. This culture dish contained a balanced salt solution (hereinafter referred to as "BSS") for medaka as supplemented with 100 U/ml of penicillin and 100 µg/mL of streptomycin [Iwamatsu, T., J. Exp. Zool. 228, 83 (1983)].

Then, unfertilized eggs to serve as cytoplasmic recipients were prepared by manipulating the thus-collected unfertilized eggs according to the following procedure.

(1) The unfertilized eggs were activated by placing them between glass electrodes filled with BSS and giving an electric stimulus (5V, 50 microseconds) at −25° C. twice repeatedly.
(2) After the lapse of 2-4 minutes after activation, the activated eggs were heat-treated in BSS at 41.5° C. for 2 minutes.
(3) After the lapse of 2 minutes, they were immediately maintained in BSS at room temperature for 5-20 minutes.
(4) After the lapse of 5 minutes, they were maintained at 10° C. until transplantation.

(Nuclear Transplantation)

The nuclear transplantation was carried out using a method fundamentally the same as the conventional methods [B. Ju et al., Develop. Growth Differ. (2003) 45, 168-169; K. Niwa et al., Develop. Growth Differ. 41, 163 (1999); K. Niwa et al., Cloning 2, 23 (2000)]. The transplantation was carried out under a stereoscopic microscope (MZAPO, Leica, Heerbrugg, Switzerland) at a magnification of 80×.

A transplantation bed was prepared by forming a V-shaped 1-mm-wide groove on 2% agar in a 60-mm plastic dish (Falcon (trade name), Becton Dickinson, Lincoln Park, N.J., USA) and filling the groove with BSS containing 100 U/ml of penicillin and 100 µg/ml of streptomycin. A micropipette for transplantation was manufactured by drawing a glass capillary with an outside diameter of 1 mm using a puller. The inside diameter of the micropipette opening was about 10-13 µm; this is the same as or slightly smaller than the diameter of the nucleus donor cell.

The specific nuclear transplantation procedure was as follows.

(1) The above-mentioned plastic dish was placed on a cooling plate (Thermo Plate; Tokai Hit) placed on the stage of the stereoscopic microscope, and the agar plate temperature was maintained at about 10° C.
(2) The unfertilized egg prepared was fixed in the V-shaped groove transplantation bed prepared so that the animal pole might turn toward the direction of the transplantation needle.
(3) The nucleus donor cells were also dispersed on the same agar plate.
(4) One nucleus donor cell was suctioned into the micropipette by a partial modification of the method for transplanting a cell into an embryo (Wakamatsu, Y, Hashimoto, H, Kinoshita, M. et al. Mol. Mar. Biol. Biotechnol. 2, 325 (1993)) using a hydraulic injector (CellTram Oil, Eppendorf, Hamburg, Germany) connected to a three-dimensional micromanipulator.
(5) The micropipette was stuck into the cytoplasm of the animal pole of the unfertilized egg and the nucleus donor cell was transplanted into the unfertilized egg.

(Fish Embryo Cultivation)

The operated eggs were transferred to a 24-well plastic plate (Sumilon, Sumitomo Bakelite), one egg in each well filled with BSS containing 2 ppm of methylene blue. The eggs were incubated at 18° C. for the first 24 hours and then at 26° C. and observed every day until hatching. After hatching, the fry were bred by the method of Wakamatsu et al. (cf. Wakamatsu, Y. (1993), op. cit.).

The identification numbers given to two fry examples that had hatched in Experiment 1 were 1NT1 and 1NT2, respectively. The identification numbers given to four fry examples that had grown after hatching in Experiment 2 were 2NT1 to 2NT4, respectively. The individuals that had matured to adult individuals after nuclear transplantation were used in a mating test and thereafter sacrificed for various evaluations.

2. Evaluations (GFP Fluorescence Detection)

The GFP fluorescence detection was carried out in all the individuals resulting from nuclear transplantation as well as in the $F_1$ generation. For GFP detection, a stereoscopic microscope (FLII, Leica) equipped with a fluorescence-producing device was used and the embryos and fish were observed for the fluorescence of GFP. The fluorescence images were photographed using a digital camera (product of Hamamatsu Photonics) mounted on the stereoscopic microscope.

(GFP Gene Detection)

A total of 14 examples, namely all the individuals resulting from nuclear transplantation, two example of the $F_1$ generation obtained from 1NT2 and OR, and 2 examples each of the $F_1$ generations obtained from 2NT1 to 2NT3 and OR, were tested for GFP gene detection.

The GFP gene detection was carried out in the following manner. First, the genomic DNA was extracted from the adult fin or the fry after hatching by a modification of the method of Blin and Stafford [N. Blin and D. M. Stafford, Nucleic Acids Res. 3, 2303 (1976)], a 20-30 ng portion thereof was used as the template for nuclear DNA amplification by PCR. For the detection (anticipated size 717 bp), the primers shown below (SEQ ID NOs:5 and 6), which are specific to the β-actin-cassette-EGFP gene, were utilized as the primers. The PCR was carried out using 0.5 unit of ExTaq DNA (Takara).

```
                                           (SEQ ID NO:5)
PR1: 5'-ATGGTGAGCAAGGGCGAGGAGCTG-3'

(SEQ ID NO:6)
PR2: 5'-CTTGTACAGCTCGTCCATGCCGAG-3'
```

For confirming the success in DNA extraction and in the subsequent PCR analysis, the endogenous EF-1α-A gene was detected by utilizing the following primers (SEQ ID NOs: 7 and 8) specific to the medaka EF-1α-A gene (anticipated size 519 bp).

```
                                           (SEQ ID NO:7)
PR3: 5'-CAGGACGTCTACAAAATCGG-3'

(DEQ ID NO:8)
PR4: 5'-AGCTCGTTGAACTTGCAGGCG-3'
```

These PCR runs were carried out in 30 cycles each consisting of 30 seconds at 94° C., 30 seconds at 60° C. and 1 minute at 72° C. The PCR products were electrophoresed on 1% agarose gel.

(Number of Chromosomes)

All the individuals resulting from nuclear transplantation were evaluated for the number of chromosomes. A tissue fragment of the caudal fin of each adult was cut into small pieces and cultured on Leibovitz's L-15 medium (Gibco) containing 20% of fetal calf serum, 100 U/ml of penicillin and 100 µg/ml of streptomycin on a four-well plastic plate (product of Nunc) coated with a 0.1% gelatin solution. After 5 days following the start of cultivation, 6 hours of treatment with 0.01% colchicin was carried out and then a chromosome preparation was prepared according to a standard procedure [T. Ladygina and Y. Wakamatsu, Fish Biol. J. MEDAKA, 10, 33 (1999)]. The number of chromosomes was checked in 10-20 cells at the metaphase.

(Mating Test)

Each adult fish resulting from nuclear transplantation was mated with OR for checking the reproductive potential thereof. Eggs were recovered from the abdomen of each female fish every day, and the eggs obtained were incubated at 26° C. in a 60-mm plastic dish filled with distilled water containing 0.5 ppm of methylene blue. They were observed for embryogenesis every day under a stereoscopic microscope. The embryogenesis in OR was employed as a control. The first generation obtained as a result of mating of each fish resulting from nuclear transplantation with OR is hereinafter referred to as $F_1$.

3. Results (Individuals Obtained by Nuclear Transplantation and Reproductive Potential)

The results of development of the individuals obtained by nuclear transplantation and showing the GFP fluorescence as obtained in Experiment 1 and Experiment 2 are shown in Table 1. As shown in Table 1, 2 eggs (0.8%) out of 250 eggs subjected to nuclear transplantation in Experiment 1 (four-somite stage embryos) hatched and matured into adult fish. In Experiment 2 (adult caudal fin-derived cultured cells), 4 eggs (0.3%) out of 1236 eggs subjected to nuclear transplantation hatched and matured into adult fish. All were female. Upon visual inspection, no particular malformations were observed in these individuals. In Experiment 1, 1NT2 alone sexually matured in 1.5 months after hatching, and the adult had about 20 eggs per laying, which was a normal roe size, and thus was normal with respect to reproductive potential and gave normal $F_1$ generation individuals. 1NT1 had no reproductive potential. Therefore, in Experiment 1, only one individual (0.4%) produced by nuclear transplantation had reproductive potential. The individuals produced by nuclear transplantation as obtained in Experiment 2 were all sexually matured in 1.5 months after hatching. Each of them had about 20 eggs per laying and the roe size was normal; they had normal reproductive potential and gave normal $F_1$ generation individuals.

At least 200 eggs were collected from each individual produced by nuclear transplantation and 95-97% of them hatched normally; 30 individuals among them were bred and 90% or more of them arrived at the adult fish stage.

TABLE 1

| Experiment No. | Donor nuclei derived from | Number of eggs submitted to nuclear transplantation | Number of individuals produced by nuclear transplantation (%) | | | |
|---|---|---|---|---|---|---|
| | | | Blastula stage | Body formation stage | Hatching | Adult fish |
| 1 | Four-somite stage embryonic cells | 250 | 34(13.6) | 18(7.2) | 2(0.8) | 2(0.8) |
| 2 | Adult caudal fin-derived cultured cells | 1236 | 331(26.8) | 89(7.2) | 4(0.3) | 4(0.3) |

Note:
The numbers for body formation stage and thereafter are numbers of individuals in which GFP fluorescence could be observed.

(GFP Fluorescence and GFP Gene)

The results of various evaluations in fish produced by nuclear transplantation and in the $F_1$ generation formed from each of them are shown in Table 2. As shown in Table 2, the GFP fluorescence was observed and the GFP gene was detected in all the individuals produced by nuclear transplantation. The GFP fluorescence was strongly expressed in the whole body of each of the individuals in the same manner as in the donor line. In the $F_1$ generation formed by 1NT2, the same GFP fluorescence as in the donor line was observed and, also, the GFP gene was detected. In the $F_1$ generations formed by 2NT1 to 2NT3 as well, the same GFP fluorescence as in the donor line was observed and the GFP gene was also detected. The endogenous EF-1α-A gene was detected, indicating that all PCR analyses were carried out properly.

TABLE 2

| Individual identification | | | | Individual produced by nuclear transplantation | | | F1 | | |
|---|---|---|---|---|---|---|---|---|---|
| Experiment | Individual | Sex | Ploidy | GFP fluorescence | GFP gene | Reproductive potential | Growth | GFP | GFP |
| Experiment 1 | 1NT1 | female | 3N | + | + | − | *1 | *1 | *1 |
| | 1NT2 | female | 2N | + | + | + | normal | + | + |
| Experiment 2 | 2NT1 | female | 2N | + | + | + | normal | + | + |
| | 2NT2 | female | 2N | + | + | + | normal | + | + |

TABLE 2-continued

| | Individual produced by nuclear transplantation | | | | | | | | |
|---|---|---|---|---|---|---|---|---|---|
| Individual identification | | | | GFP | GFP | Reproductive | F1 | | |
| Experiment | Individual | Sex | Ploidy | fluorescence | gene | potential | Growth | GFP | GFP |
| | 2NT3 | female | 2N | + | + | + | normal | + | + |
| | 2NT4 | female | 2N | + | + | + | normal | + | *2 |

*1: Confirmation impossible since no F1 generation was obtained.
*2: Not confirmed since the F1 generation was young.

Such modes of expression of the GFP fluorescence and GFP gene suggested the possibility of the donor nucleus-derived chromosomes being retained dominantly in the individuals produced by nuclear transplantation, and in particular the possibility of those chromosomes being retained dominantly or those chromosomes alone being retained in reproductive cells.

(Chromosomal Ploidy)

All the individuals produced by nuclear transplantation were checked for the number of chromosomes and evaluated for the ploidy. In all the individuals, the number was 48, hence they were diploids, except for 1NT1 which was a triploid, with the number being 76.

The results mentioned above revealed that the nuclear transplantation carried out in this example can give fish embryos and individuals having a correct chromosomal ploidy and reproductive potential and expressing genes on the donor chromosomes. Considering the prior art results of the nuclear transplantation (activation by transplantation) of caudal fin tissue-derived cultured cells into unfertilized eggs, namely the results that mosaicism was encountered with respect to the chromosomal ploidy and no mature individuals were obtained. Further, the gene expression on the donor nucleus-derived chromosomes was also mosaic, it is evident that the temperature stress imposed after activation in this example contributed to the production of fish embryos and individuals having a correct chromosomal ploidy and reproductive potential and expressing genes on the donor nucleus chromosomes.

EXAMPLE 2

Investigations Concerning Conditions for Retention of the Second Polar Body Release by High Temperature Treatment Female fishes that have been laying eggs everyday were transferred to an isolation tank on the day before experiment. On the day of experiment, they were dissected within 1-2 hours from the start of the light period and mature unfertilized eggs were recovered from ovaries. On the other hand, males were dissected, testes were excised and the tissues were squashed in BSS to give a sperm suspension. Unfertilized eggs were placed in 50 µl of BSS in an Eppendorf tube and a portion of the sperm suspension was added thereto for insemination. The tube was maintained at 25° C. for a predetermined period and then transferred to a water bath at 37° C. or 41° C. and maintained at either of the predetermined temperatures for a predetermined period. After this treatment, the eggs were transferred into BSS in a plastic culture dish and allowed to develop in an incubator at 26° C. for 5-7 days. The thus-obtained embryos were deprived of the chorion by means of forceps, and a cell suspension was prepared by gently pipetting the embryonic bodies in 1 ml of Eagle's MEM medium. The nucleus of each of these cells was stained with 4-6-diamino-2-phenylindole dihydrochloride (DAPI) and submitted to a flow cytometer (Ploidy Analyser, product of Partec, Germany) for cellular ploidy analysis.

In this experiment, the time for maintenance at 25° C. after insemination included three periods, namely, 90 seconds, 135 seconds and 180 seconds. The time of the subsequent high temperature treatment was 10 minutes or 15 minutes in the case of 37° C., and 2 minutes in the case of 41° C. In control runs, eggs were inseminated in the same manner as in the experiment groups and maintained in an incubator at 26° C. for development. For each set of experiment conditions, 20-45 unfertilized eggs were used. The sets of experiment conditions are shown in Table 3.

TABLE 3

| Treatment temperature (° C.) | Time after insemination (sec.) | High temperature treatment time (min.) | Haploid (%) | Diploid (%) | Triploid (%) | Death etc. (%) |
|---|---|---|---|---|---|---|
| 37 | 90 | 10 | 0 | 40 | 3 | 57 |
| 37 | 90 | 15 | 0 | 37 | 3 | 60 |
| 37 | 180 | 10 | 0 | 47 | 0 | 53 |
| 37 | 180 | 15 | 0 | 33 | 3 | 64 |
| 41 | 90 | 2 | 0 | 39 | 0 | 61 |
| 41 | 135 | 2 | 0 | 47 | 16 | 37 |
| 41 | 180 | 2 | 0 | 26 | 22 | 52 |

Since untreated sperms were used for insemination in this experiment, it was considered that embryos may become triploids if the second polar body release could be suppressed. Therefore, the conditions for enabling efficient production of triploids were investigated. The results are shown in Table 3. As shown in Table 3, even the temperature treatment at 37° C. gave triploids although the percentage was low (3%). In the case of treatment at 41° C., high percentage of triploids was found in the experiment groups subjected to temperature treatment after the lapse of 135 seconds or 180 seconds following insemination. In these groups, the yields of triploids were 16-22%. In the control runs, at least 95% of the eggs developed normally and all were diploids. The above results thus revealed that it is possible to use a temperature of 37° C. or higher as the temperature for high temperature treatment and that a temperature in the vicinity of 41° C. can be used.

EXAMPLE 3

Investigations Concerning Conditions for Retention of the Second Polar Body Release by Low Temperature Treatment Female fishes that have been laying eggs everyday were transferred to an isolation tank on the day before experiment. On the day of experiment, they were dissected within 1-2 hours from the start of the light period and mature unfertilized eggs (unfertilized eggs) were recovered from ovaries. On the other hand, males were dissected, testes were excised and the tissues were squashed in BSS to give a sperm suspension. Unfertilized eggs were placed in 50 μl of BSS in an Eppendorf tube and a portion of the sperm suspension was added thereto for insemination. The tube was maintained at 25° C. for a predetermined period and then immediately transferred onto ice and maintained at 0° C. for a predetermined period. After this treatment, the eggs were transferred into BSS in a plastic culture dish and allowed to develop in an incubator at 26° C. for 5-7 days. The thus-obtained embryos were deprived of the chorion by means of forceps, and a cell suspension was prepared by gently pipetting the embryonic bodies in 1 ml of Eagle's MEM medium. The nucleus of each of these cells was stained with 4-6-diamino-2-phenylindole dihydrochloride (DAPI) and submitted to a flow cytometer (Ploidy Analyser, product of Partec, Germany) for cellular ploidy analysis.

In this experiment, the time for maintenance at 25° C. after insemination included five periods: 60 seconds, 90 seconds, 105 seconds, 120 seconds and 180 seconds. The time of the subsequent low temperature treatment on ice was 10 minutes, 15 minutes or 20 minutes. In control runs, eggs were inseminated in the same manner as in the experiment groups and maintained in an incubator at 26° C. for development. For each set of experiment conditions, 20-45 unfertilized eggs were used. The sets of experiment conditions are shown in Table 4.

TABLE 4

| Treatment temperature (° C.) | Time after insemination (sec.) | Low temperature treatment time (min.) | Haploid (%) | Diploid (%) | Triploid (%) | Death etc. (%) |
| --- | --- | --- | --- | --- | --- | --- |
| 0 | 60 | 10 | 5 | 10 | 45 | 40 |
| 0 | 60 | 15 | 0 | 0 | 37 | 63 |
| 0 | 60 | 20 | 5 | 0 | 32 | 63 |
| 0 | 90 | 10 | 7 | 36 | 14 | 43 |
| 0 | 90 | 15 | 0 | 11 | 33 | 56 |
| 0 | 90 | 20 | 0 | 0 | 44 | 56 |
| 0 | 105 | 10 | 5 | 65 | 25 | 5 |
| 0 | 105 | 15 | 21 | 5 | 47 | 27 |
| 0 | 105 | 20 | 20 | 10 | 25 | 45 |
| 0 | 120 | 10 | 0 | 13 | 17 | 70 |
| 0 | 120 | 15 | 13 | 4 | 13 | 70 |
| 0 | 120 | 20 | 0 | 4 | 21 | 75 |
| 0 | 180 | 10 | 11 | 34 | 24 | 31 |
| 0 | 180 | 15 | 4 | 25 | 18 | 53 |
| 0 | 180 | 20 | 4 | 17 | 25 | 54 |

Since untreated sperms were used for insemination in this experiment, it was considered that embryos became triploids if the second polar body release could be suppressed. Therefore, the conditions for enabling efficient production of triploids were investigated. The results are shown in Table 4. High percentage of triploids could be produced in the experiment groups subjected to 10-20 minutes of low temperature treatment at 0° C. after the lapse of 60 seconds to 105 seconds following insemination. In these groups, the yields of triploids were 44-47%. In the control runs, at least 95% of the eggs developed normally and all were diploids. The above results revealed that a temperature in the vicinity of 0° C. can be used as the temperature for the low temperature treatment.

EXAMPLE 4

Detailed Investigations Concerning High Temperature Treatment Conditions

In this example, first, unfertilized eggs were inseminated with untreated sperms and then subjected to high temperature treatment (41° C., 2 minutes) at various timings, namely from one minute and 30 seconds to 3 minutes 30 seconds after insemination (temperature: 25° C.) to find out the best timing for subjecting the recipient eggs after activation to the high temperature treatment. Otherwise in the same manner as in Example 2, the rates of success in diploidization (experimentally triploidization because of insemination with untreated sperms) owing to retention of the second polar body release were examined.

TABLE 5

| Time after insemination | Number of eggs treated | Deaths | Ploidy of embryos developed | | |
| --- | --- | --- | --- | --- | --- |
| | | | 1N | 2N | 3N |
| 1'30" | 60 | 9(15.0) | 0(0) | 40(66.7) | 11(18.3) |
| 1'45" | 59 | 7(11.9) | 0(0) | 45(76.3) | 7(11.9) |
| 2' | 67 | 31(46.3) | 2(3.0) | 12(17.9) | 22(32.8) |
| 2'15" | 62 | 27(43.5) | 1(1.6) | 23(37.1) | 11(17.7) |
| 2'30" | 60 | 15(25.0) | 1(1.7) | 16(26.7) | 28(46.7) |
| 2'45" | 59 | 10(16.9) | 2(3.4) | 6(10.2) | 41(69.5) |
| 3' | 60 | 22(36.7) | 0(0) | 25(41.7) | 13(21.7) |
| 3'30" | 53 | 13(24.5) | 2(3.8) | 38(71.7) | 0(0) |

The figures in the parentheses indicate percentage values.

As shown in Table 5, the rate of success in diploidization (in the table, triploidization) was highest at 69.5% when the high temperature treatment was carried out after the lapse of 2 minutes and 45 seconds following activation. Based on the above results, the above conditions (time and storage temperature) for storing recipient eggs after activation until high temperature treatment were selected.

(Additional Experiment (Referred to as "Experiment 3") Under High Temperature Treatment Conditions Selected)

Then, adult caudal fin cultured cells were used as donors. Recipient unfertilized eggs were stored after activation until high temperature treatment under the above-mentioned storage time and temperature conditions (2 minutes and 45 seconds, 25° C.), then subjected to high temperature treatment and, thereafter, maintained at 25° C. for 20 minutes and then stored at 10° C. until nuclear transplantation. Otherwise in the same manner as in Example 1, fish embryos were prepared by nuclear transplantation and caused to hatch, followed by mating. The results of development of individuals produced by nuclear transplantation in Experiment 3 are shown in Table 6. Further, the characteristics of the individuals obtained by nuclear transplantation in Experiment 2 in Example 1 (individual numbers: 2N1 to 2N4) and of the individuals obtained by nuclear transplantation in Experiment 3 (3N1 to 3N7) as well as the results of evaluations of the $F_1$ generations derived from these individuals are shown in Table 7 and Table 8.

TABLE 6

| Donor nuclei derived from | Number of eggs submitted to nuclear transplantation | Number of individuals produced by nuclear transplantation (%) | | | |
|---|---|---|---|---|---|
| | | Blastula stage | Body formation stage | Hatching | Adult fish |
| Adult caudal fin-derived cultured cells | 798 | 255(32.0) | 141(17.7) | 11(1.4) | 7(0.9) |

Note:
The numbers for embryogenesis stage and thereafter are numbers of individuals in which GFP fluorescence could be observed.
( ): %

TABLE 7

Individual produced by nuclear transplantation (Adult fish)

| Individual No. | Sex | Ploidy | GFP fluorescence | Mosaicism | Reproductive potential |
|---|---|---|---|---|---|
| 2NT1 | female | 2N | + | − | + |
| 2NT2 | female | 2N | + | − | + |
| 2NT3 | female | 2N | + | − | + |
| 2NT4 | female | 2N | + | − | + |
| 3NT1 | female | 2N | + | − | + |
| 3NT2 | male | ND | + | − | ND |
| 3NT3 | female | 2N | + | − | + |
| 3NT4 | male | 2N | + | − | + |
| 3NT5 | male | 2N | + | − | − |
| 3NT6 | female | 2N + 3N | + | − | + |
| 3NT7 | male | 2N | + | − | + |

3NT2 died before reproductive potential and ploidy examinations.

TABLE 8

| | | F1(F0 × red medaka) | | | F2(F1 × red medaka) | | |
|---|---|---|---|---|---|---|---|
| F0 | | Number of embryos examined | GFP expression | | Number of embryos examined | GFP expression | |
| Individual No. | Sex | | + | − | | + | − |
| 2NT1 | female | 356 | 356(100) | 0 | 598 | 292(48.8) | 306(51.2) |
| 2NT2 | female | 312 | 312(100) | 0 | 637 | 309(48.5) | 328(51.5) |
| 2NT3 | female | 232 | 232(100) | 0 | 661 | 336(50.8) | 325(49.2) |
| 2NT4 | female | 381 | 381(100) | 0 | 720 | 367(51.0) | 353(49.0) |
| 3NT1 | female | 359 | 359(100) | 0 | 657 | 331(50.4) | 326(49.6) |
| 3NT3 | female | 374 | 374(100) | 0 | 656 | 333(50.8) | 323(49.2) |
| 3NT4 | male | 84 | 84(100) | 0 | 602 | 301(50.0) | 301(50.0) |
| 3NT6 | female | 14 | 14(100) | 0 | 322 | 157(48.8) | 165(51.2) |
| 3NT7 | male | 210 | 210(100) | 0 | 710 | 377(53.1) | 333(46.9) |
| total | | 2322 | 2322(100) | 0 | 5563 | 2803(50.4) | 2760(49.6) |

As shown in Table 6, adult fish could be obtained in a final yield of 0.9%. Further, as shown in Table 7, the GFP gene was expressed uniformly in the whole body in each of the total of 11 adult fish obtained in Experiment 2 and Experiment 3, 9 individuals were diploids and, in 8 individuals, fertility was confirmed. One individual was a diploid-triploid mosaic but showed weak fertility. Furthermore, as shown in Table 8, the donor marker GFP was expressed in all the $F_1$ embryos obtained by the mating experiment using the total of 9 individuals whose fertility had been confirmed and, furthermore, the GFP expression was observed in half of the $F_2$ embryos; thus, the donor marker had been transmitted to the daughter and granddaughter generations through Mendel's law.

The above results revealed that adult fish cultured cells also can provide individuals by nuclear transplantation at a success rate of about 1%. Further, it was revealed that the donor nuclear chromosomes selectively constitute the chromosomes of the individuals produced by nuclear transplantation, so that the donor nucleus-derived characteristics can be reliably expressed in the individuals obtained by nuclear transplantation.

INDUSTRIAL APPLICABILITY

The present invention can be utilized in fish researches and productions and, further, in tests and diagnoses using fish, among others.

Sequence Listing Free Text
SEQ ID NO:1 to SEQ ID NO:8: Synthetic primers

---

What is claimed is:

1. A method for preparing fish embryos comprising:
   activating an unfertilized egg;
   imposing a physical and/or chemical stress that inhibits or suppresses second polar body release on said activated egg; and
   transplanting a fish cell nucleus of the same species as said unfertilized egg into said activated and stress treated egg.

2. A method for preparing fish embryos as in claim 1, wherein the physical and/or chemical stress is a stress that causes chromosome diploidization in the unfertilized egg having started development.

3. A method for preparing fish embryos as in claim 1, wherein said physical and/or chemical stress includes at least a stress due to the temperature of the environment surrounding the unfertilized egg.

4. A method for preparing fish embryos as in claim 1, wherein the activating stimulation involves no fish cell nucleus transplantation.

5. A method for preparing fish embryos as in claim 4, wherein the stimulus activating the unfertilized egg is an electric stimulus.

6. A method for preparing fish embryos as in claim 1, wherein the unfertilized egg to be fed while imposing a physical and/or chemical stress retains the endogenous nucleus thereof.

7. A method for preparing fish embryos as in claim 1, wherein a cell that feeds said cell nucleus to be transplanted into the unfertilized egg is selected from among somatic cells and cultured cells.

8. A method for preparing fish embryos as in claim 1, wherein a cell nucleus feeding cell is selected from among embryonic cells.

9. A method for preparing fish embryos comprising:
   imposing, on an endogenous nucleus-retaining unfertilized egg, a stimulus that activates said unfertilized egg,
   imposing a physical and/or chemical stress that causes chromosome diploidization in the activated egg that has started development or a physical and/or chemical stress equivalent to such degree; and then
   transplanting a fish somatic cell-derived or cultured cell-derived cell nucleus into the activated and stress treated egg.

10. A method for preparing fish embryos as in claim 1, wherein a cell nucleus feeding cell carries one or more members selected from among DNA mutations and foreign DNAs on a chromosome or chromosomes thereof.

11. A method for preparing fish embryos as in claim 1, wherein fish is selected from among fish species belonging to the genus *Oryzias*.

12. A method for preparing fish embryos as in claim 1, wherein the fish embryo is a diploid.

13. A method for preparing fish embryos as in claim 1, wherein the individual obtained from the fish embryo has a cell retaining only the chromosomes derived from a cell nucleus feeding cell.

14. A method for preparing fish embryos as in claim 13, wherein the cell retaining only the chromosomes derived from the cell nucleus feeding cell transplanted is a reproductive cell.

15. A method for preparing fish embryos as in claim 1, further including storing said activated egg from after having been activated until the physical and/or chemical stress is imposed under storage conditions that have been determined in advance.

16. A method for preparing fish embryos as in claim 15, wherein the ploidy of the fish embryo to be obtained is adjusted through the storage conditions determined in advance.

17. A method for producing fish individuals comprising:
    a method for preparing fish embryos as in claim 1 and
    causing the prepared embryo to develop until hatching.

18. The method of claim 17, further comprising breeding the hatched fish.

19. A method for producing a transgenic fish comprising:
introducing a foreign DNA into a fish cell to thereby obtain a fish cell having the foreign DNA on a chromosome thereof;
preparing a fish embryo by transplanting the fish cell nucleus having the foreign DNA introduced on the chromosome thereof into an unfertilized egg; and
causing the embryo to develop until hatching;
wherein the fish embryo preparation step includes imposing a physical and/or chemical stress that inhibits or suppresses second polar body release on said unfertilized egg.

* * * * *

```
                        SEQUENCE LISTING

<160> NUMBER OF SEQ ID NOS: 8

<210> SEQ ID NO 1
<211> LENGTH: 33
<212> TYPE: DNA
<213> ORGANISM: Artificial Sequence
<220> FEATURE:
<223> OTHER INFORMATION: Synthetic construct

<400> SEQUENCE: 1
ctgtagcggc cgcacagact ttctcctccc cag                              33

<210> SEQ ID NO 2
<211> LENGTH: 41
<212> TYPE: DNA
<213> ORGANISM: Artificial Sequence
<220> FEATURE:
<223> OTHER INFORMATION: Synthetic construct

<400> SEQUENCE: 2
tgcgtctaga cgcatatgtt aagctttaaa gaatcaatgg a                     41

<210> SEQ ID NO 3
<211> LENGTH: 35
<212> TYPE: DNA
<213> ORGANISM: Artificial Sequence
<220> FEATURE:
<223> OTHER INFORMATION: Synthetic construct

<400> SEQUENCE: 3
tatggcatgc catatggtga atgtatagta gcgta                            35

<210> SEQ ID NO 4
<211> LENGTH: 38
<212> TYPE: DNA
<213> ORGANISM: Artificial Sequence
<220> FEATURE:
<223> OTHER INFORMATION: Synthetic construct

<400> SEQUENCE: 4
tcaaggtacc aagaattcgg ctaaactgga aaagaaca                         38

<210> SEQ ID NO 5
<211> LENGTH: 24
<212> TYPE: DNA
<213> ORGANISM: Artificial Sequence
<220> FEATURE:
<223> OTHER INFORMATION: Synthetic construct

<400> SEQUENCE: 5
atggtgagca agggcgagga gctg                                        24

<210> SEQ ID NO 6
<211> LENGTH: 24
<212> TYPE: DNA
<213> ORGANISM: Artificial Sequence
<220> FEATURE:
<223> OTHER INFORMATION: Synthetic construct
```

```
<400> SEQUENCE: 6
cttgtacagc tcgtccatgc cgag                                              24

<210> SEQ ID NO 7
<211> LENGTH: 20
<212> TYPE: DNA
<213> ORGANISM: Artificial Sequence
<220> FEATURE:
<223> OTHER INFORMATION: Synthetic construct

<400> SEQUENCE: 7
caggacgtct acaaaatcgg                                                   20

<210> SEQ ID NO 8
<211> LENGTH: 21
<212> TYPE: DNA
<213> ORGANISM: Artificial Sequence
<220> FEATURE:
<223> OTHER INFORMATION: Synthetic construct

<400> SEQUENCE: 8
agctcgttga acttgcaggc g                                                 21
```